US011457586B2

(12) United States Patent
Brown et al.

(10) Patent No.: US 11,457,586 B2
(45) Date of Patent: Oct. 4, 2022

(54) WATERMELON LINE 'WL0005'

(71) Applicant: Enza Zaden Beheer B.V., Enkhuizen (NL)

(72) Inventors: Laura Barham Brown, Gilroy, CA (US); Robert Barham, Gilroy, CA (US)

(73) Assignee: Enza Zaden Beheer B.V., Enkhuizen (NL)

( * ) Notice: Subject to any disclaimer, the term of this patent is extended or adjusted under 35 U.S.C. 154(b) by 0 days.

(21) Appl. No.: 16/994,304

(22) Filed: Aug. 14, 2020

(65) Prior Publication Data
US 2022/0046884 A1 Feb. 17, 2022

(51) Int. Cl.
*A01H 6/34* (2018.01)
*A01H 5/08* (2018.01)

(52) U.S. Cl.
CPC .............. *A01H 6/342* (2018.05); *A01H 5/08* (2013.01)

(58) Field of Classification Search
None
See application file for complete search history.

(56) References Cited

U.S. PATENT DOCUMENTS

| | | | |
|---|---|---|---|
| 5,777,196 A | 7/1998 | Hall | |
| 5,948,957 A | 9/1999 | Chapko et al. | |
| 5,959,185 A | 9/1999 | Streit et al. | |
| 5,969,212 A | 10/1999 | Getschman | |
| 5,973,234 A | 10/1999 | Mueller et al. | |
| 5,977,445 A | 11/1999 | Soper et al. | |
| 9,066,477 B2 * | 6/2015 | Juarez | C12N 15/8201 |
| 9,066,478 B2 * | 6/2015 | Juarez | A01H 4/00 |
| 9,066,482 B1 * | 6/2015 | Juarez | A01H 1/04 |
| 9,408,354 B2 * | 8/2016 | de Groot | A01H 5/08 |
| 9,545,065 B2 | 1/2017 | Barham et al. | |
| 9,848,548 B1 * | 12/2017 | Bernier | C12N 15/8241 |
| 9,955,638 B2 | 5/2018 | Chang | |
| 10,098,297 B2 * | 10/2018 | Juarez | A01H 1/02 |
| 10,687,495 B2 | 6/2020 | de Groot | |
| 11,026,385 B2 | 6/2021 | Barham Brown et al. | |
| 2018/0139920 A1 * | 5/2018 | Chang | A01H 6/342 |
| 2019/0343063 A1 * | 11/2019 | Chang | A01H 5/08 |
| 2020/0154665 A1 | 5/2020 | Brown et al. | |
| 2020/0375138 A1 | 12/2020 | Barham Brown et al. | |
| 2022/0022403 A1 | 1/2022 | Brown et al. | |
| 2022/0022404 A1 | 1/2022 | Brown et al. | |

OTHER PUBLICATIONS

Enza Zaden (Oct. 2017, "Red Amber (E26C.00036)", http://webkiosk.enzazaden.com/leaflet-watermelon-red-Amber-2018/59618782).*
Ernest et al (2018, Seedless Watermelon Trials 2017, University of Delaware Cooperative Extension, https://sites.udel.edu/weeklycropupdate/?p=1 1482).*
Guan (2018, Top Performing Watermelon Varieties in the 2017 Indiana Watermelon Variety Trial, Purdue University, https://vegcropshotline.org/article/top-performing-watermelon-varieties-in-the-2017-indiana-watermelon-variety-trial/).*
Compton et al., (1993). Shoot Organogenesis and Plant Regeneration from Cotyledons of Diploid, Triploid, and Tetrapioid Watermelon, J. Amer. Soc. Hort. Sci., 118(1):151 -157.
Coolong, Timothy (2015). "Trial Report: Seedless Watermelon Variety Evaluation—2015," Available online at <https://site.extension.uga.edu/colquittag/files/2016/01/2015-UGA-Tifton-Watermelon-Variety-Trial-Results.pdf>, 12 pages.
Enza Zaden USA, Inc. Jan. 2020. 'Red Amber', 'Red Garnet', and 'Cracker Jack' Vegetable Seed Catalogue USA & Canada 2020. Available online at <https://webkiosk.enzazaden.com/catalogue-usa-2020/62983894>, Obtained on Jul. 24, 2020. p. 48.
Enza Zaden, "Cracker Jack (E26C.00063)", leaflet as of Nov. 2019, Available online at <http://webkiosk.enzazaden.com/leaflet-cracker-jack019/62935919>, 1 page.
Enza Zaden, "Enza Zaden Field Day: May 14, 2019", website as of Apr. 12. 2019, Available online at <https://www.enzazaden.com/us/news-and-events/news/enza-zaden-field-day-May 14>, Obtained on Feb. 2, 2020, 2 pages.
Enza Zaden, "Red Amber (E26C.00036)", leaflet as of Oct. 2017, Available online at <http://webkiosk.enzazaden.com/leaflet-watermelon-red-amber-2018/59618782>, 1 page.
Enza Zaden, "Red Garnet (E26C.00034)", leaflet as of Dec. 2017, Available online at <http://webkiosk.enzazaden.com/leaflet-watermelon-red-garnet-2018/59586596>. 1.132 Declaration included. 3 pages.
Enza Zaden, "Red Opal (E26C.00035)", leaflet as of Oct. 2017, Available online at <http://webkiosk.enzazaden.com/leaflet-watermelon-red-opal-2018/59618793>, 1 page.
Enza Zaden, (2019). "Gilroy Watermelon Field Day, Aug. 20, 2019", Enza Zaden USA, Inc., 2 pages.
Enza Zaden, (2019). "Redefining the watermelon industry, Field Day 2019", Enza Zaden USA, Inc., 4 pages.
Guan et al. (2015). "Midwest Triploid Watermelon Variety Trial in Southwest Indiana—2015," Available online at <https://ag.purdue.edu/arge/swpap/Documents/2015%20seedless%20watermelon%20variety%20trial%20report%20at%20Southwest%20IN.pdf>, 12 pages.
Guan et al. (2018). "2018 Watermelon Variety Evaluation in Indiana," Available online at <https://ag.purdue.edu/arge/swpap/Documents/2018%20Watermelon%20Variety%20Evaluation%20in%20Indiana_.pdf>, 37 pages.
Syngenta, (2017). "Watermelon Crop Guide," pp. 1 and 6. Syngenta US, 2 pages.
Unpublished U.S. Appl. No. 16/934,752, filed Jul. 21, 2020, titled "Watermelon Variety 'Cracker Jack',".
Unpublished U.S. Appl. No. 16/934,773, filed Jul. 21, 2020, titled "Watermelon Line 'WL0002',".
Unpublished U.S. Appl. No. 16/998,768, filed Aug. 20, 2020, titled "Watermelon Variety 'Red Amber',".

(Continued)

*Primary Examiner* — Anne Kubelik
(74) *Attorney, Agent, or Firm* — Morrison & Foerster LLP

(57) ABSTRACT

A new watermelon line designated 'WL0005' is described. 'WL0005' is a watermelon line exhibiting stability and uniformity.

8 Claims, 2 Drawing Sheets
(2 of 2 Drawing Sheet(s) Filed in Color)

(56) References Cited

OTHER PUBLICATIONS

Berry et al., (2003). "Assessing Probability of Ancestry Using Simple Sequence Repeat Profiles: Applications to Maize Inbred Lines and Soybean Varieties," Genetics, 165:331-342.

Cregan et al., (1999). "An Integrated Genetic Linkage Map of the Soybean Genome," Crop Science, 39:1464-1490.

Ernest, E. (2018). "Seedless Watermelon Trials 2017," available online at <https://sites.udel.edu/weeklycropupdate/?p=11482>, 4 pages.

Guan, W. (2018). "Top Performing Watermelon Varieties in the 2017 Indiana Watermelon Variety Trial," available online at <https://vegcropshotline.org/article/top-performing-watermelon-varieties-in-the-2017-indiana-watermelon-variety-trial/>, 2 pages.

Johnson et al., (2019). "Seedless Watermelon Variety Trial Results 2019," University of Delaware Elbert N. & Ann V. Carvel Research and Education Center, 28 pages.

Ren et al., (2014). "An integrated genetic map based on four mapping populations and quantitative trait loci associated with economically important traits in watermelon (*Citrullus lanatus*)," BMC Plant Biology, 14:33, 11 pages.

Unpublished U.S. Appl. No. 17/164,614, filed Feb. 1, 2021 titled "Watermelon Line 'WL0044',".

Clemson University, Published on Feb. 22, 2021. "Seedless Watermelon Variety Trial @ EREC<2021," available online at <https://www.clemson.edu/cafls/research/edisto/erecwatermelonvarietytrialreport2021.pdf>, 8 pages.

Guan et al., (2020). "2019 Standard-size and Personal-size Triploid Watermelon Variety Evaluation in Indiana," Southwest Purdue Agricultural Center, 31 pages.

Guan et al., Published on Nov. 2021. "2021 Standard-size Triploid Watermelon Variety Evaluation in Indiana," available online at <https://docs.lib.purdue.edu/cgi/viewcontent.cgi?article=1227&context=mwvtr>, 32 pages.

* cited by examiner

WATERMELON LINE 'WL0005'

FIELD OF THE INVENTION

The present invention relates to the field of plant breeding. In particular, this invention relates to a new watermelon, *Citrullus lanatus*, line designated 'WL0005'.

BACKGROUND OF THE INVENTION

All cultivated forms of watermelon belong to the polymorphic species *Citrullus lanatus*. As a crop, watermelons are grown commercially wherever environmental conditions permit the production of an economically viable yield. Cultivated watermelons grow as annual plants with large, broad leaves. The leaves may be lobed or simple and are typically orbicular to triangular-ovate in shape. The flowers are monoecious, producing both male and female flowers. The flesh color of cultivated watermelons is red, yellow, or white with ovate to oblong strongly compressed seeds that may be brown or white in color. The characterization of the mature fruit can vary widely among varieties of watermelon. Fruits may be round to oblong or elliptical with rind colors varying from dark green to yellow and rind patterning varying widely.

Many changes that occurred with the domestication of the watermelon relate to fruit morphology, with a specialization in fruit shape, size, and flavor. Cultivated watermelons can vary from 5 to 45 pounds, depending on the variety or line. In the United States, watermelon is grown in at least 44 states, but the principal watermelon growing states are Georgia, Florida, Texas, and California. Asia is the largest producer of watermelon, with 83.4% of the world production in 2011. Fresh watermelons are consumed in many forms, generally fresh, sliced, or as an ingredient in prepared foods. Over 80% of watermelons grown in the United States are triploid seedless varieties, preferred for their ease of consumption, increased yield, and premium market value over diploid seeded varieties.

*Citrullus lanatus* is a member of the family Cucurbitaceae, which contains about 90 genera and 700 to 760 species. The family includes melons, pumpkins, squashes, gourds, cucumber, loofah, and many weeds. The genus *Citrullus*, to which the watermelon belongs, consists of about four species, including *C. colocynthis, C. rehmii,* and *C. ecirrhosus*, all of which may be crossed with each other successfully. The watermelon is believed to be native to southern Africa and has been cultivated there for about 4000 years.

Regular, seeded watermelon is diploid and has eleven pairs of chromosomes (2n=2x=22). There also exist tetraploid varieties, which have 44 chromosomes in their somatic cells (2n=4x=44). Popular "seedless" varieties are triploid, meaning they have 33 chromosomes in their somatic cells (3x=33) and are derived from a cross between male diploid and female tetraploid parents. Triploid plants are unable to produce viable gametes; therefore, when triploid plants are grown in the presence of diploid plants, the triploid plants produce seedless fruit. These seedless varieties may sometimes produce fruit with small, edible white ovules, similar to those in immature cucumbers.

Watermelon is an important and valuable field crop with an array of observable and detectable traits of importance both to watermelon consumers and watermelon growers. Traits of importance include taste, texture, size, rind patterns, and shapes. Watermelon consumers desire watermelons that have excellent taste and sweetness. In addition, the texture and firmness of flesh is critical to the consumer experience of eating watermelons. Watermelon fruit comes in a wide range of sizes, from as small as one kilogram up to twenty or more kilograms, with the main commercial range being from approximately three kilograms up to approximately twelve kilograms. There are dozens of rind patterns possible on watermelon fruit. While consumers tend to prefer particular rind patterns, novel rind patterns can also lead to fruit purchase. Watermelon fruit can have an array of shapes from round to oval (length/width ratios up to 3:1). Consumers have distinct preferences for fruit shape. Growers also can have preferences for fruit shape as, for example, in some markets a blocky shape is considered easier to ship than a round shape. Growers also are highly focused on having high yields from their watermelon fields. At the same time, growers must meet quality standards for their crops to be accepted by wholesale buyers and shippers, including producing fruit free of defects such as hollow-heart, internal growth, not having "seeds" in the seedless triploid hybrids, sufficiently good color, and good appearance of fruit. Moreover, for both quality and yield, growers often need certain disease resistances for their watermelon varieties.

In spite of many genetic improvements to watermelons for both growing and consumption, the consumer experience of watermelons is often disappointing. This is largely due to watermelon being a commodity in the marketplace, with watermelons coming from many different growers and being sold based on a wholesale price rather than taste quality. In addition, current watermelon breeding is focused on producing watermelons that look similar to other watermelons in the marketplace. Thus, there is a need to provide watermelon varieties or lines with improved taste that have distinguishing features (such as distinct rind patterns), which will satisfy grower requirements and provide easily recognizable and better-tasting watermelons for consumers.

SUMMARY OF THE INVENTION

In order to meet these needs, the present invention is directed to watermelon varieties or lines with improved taste and distinguishing features, such as light medium green rind pattern and rich flesh coloration. In addition, the present invention is directed to watermelon varieties or lines with improved firmness of flesh and improved holding ability in the field.

In one embodiment, the present invention is directed to a tetraploid inbred watermelon line, *Citrullus lanatus*, seed designated as 'WL0005' having NCIMB Accession Number 43650. In one embodiment, the present invention is directed to a *Citrullus lanatus* watermelon plant and parts isolated therefrom produced by growing 'WL0005' watermelon seed. In another embodiment, the present invention is directed to a *Citrullus lanatus* plant and parts isolated therefrom having all the physiological and morphological characteristics of a *Citrullus lanatus* plant produced by growing 'WL0005' watermelon seed having NCIMB Accession Number 43650.

Watermelon plant parts include watermelon leaves, ovules, pollen, seeds, watermelon fruits, parts of watermelon fruits, flowers, cells, and the like. In another embodiment, the present invention is further directed to watermelon leaves, ovules, pollen, seeds, watermelon fruits, parts of watermelon fruits, and/or flowers isolated from 'WL0005' watermelon plants. In certain embodiments, the present invention is further directed to pollen or ovules isolated from 'WL0005' watermelon plants. In another embodiment, the present invention is further directed to protoplasts produced from 'WL0005' watermelon plants. In another embodiment, the present invention is further directed to tissue culture of 'WL0005' watermelon plants, and to watermelon plants regenerated from the tissue culture, where the plant has all of the morphological and physiological characteristics of 'WL0005' watermelon. In certain embodiments, tissue culture of 'WL0005' watermelon plants is produced from a plant part selected from leaf, anther, pistil, stem, petiole, root, root tip, fruit, seed, flower, cotyledon, hypocotyl, embryo, and meristematic cell.

In yet another embodiment, the present invention is further directed to a method of selecting watermelon plants, by a) growing 'WL0005' watermelon plants where the 'WL0005' plants are grown from watermelon seed having NCIMB Accession Number 43650, and b) selecting a plant from step a). In another embodiment, the present invention is further directed to watermelon plants, plant parts and seeds produced by the watermelon plants where the watermelon plants are isolated by the selection method of the invention.

According to the invention, there is provided a watermelon plant designated 'WL0005'. This invention thus relates to the seeds of watermelon 'WL0005' and to the plants of watermelon 'WL0005'. This invention also relates to methods for producing other watermelon cultivars or hybrids derived from watermelon 'WL0005' and to the watermelon cultivars and hybrids derived by the use of those methods.

The invention further provides triploid watermelon seed and triploid watermelon plants (and parts thereof, such as seedless fruit) produced by crossing watermelon line 'WL0005' with a diploid plant. Optionally, 'WL0005' is used as the female parent.

In another embodiment, the invention provides a method of producing triploid watermelon seed, the method including: (a) crossing a watermelon plant of line 'WL0005' with a diploid watermelon plant; and (b) optionally, harvesting the resultant triploid watermelon seed. In some embodiments, the plant of line 'WL0005' is the female parent and the diploid parent is the male plant (i.e., pollinator). Also provided is a hybrid triploid watermelon seed produced by the foregoing method, and a triploid watermelon plant (and parts thereof, including seedless fruit) grown from the triploid seed. In another embodiment, the present invention is further directed to watermelon leaves, ovules, pollen, seeds, watermelon fruits, parts of watermelon fruits, and/or flowers isolated from hybrid triploid watermelon plants.

In still a further embodiment, the invention provides a tetraploid watermelon plant, or a part thereof, produced by crossing a 'WL0005' plant with a different tetraploid watermelon plant (e.g., a tetraploid inbred or hybrid plant).

In another embodiment, the present invention is directed to single gene converted plants of watermelon 'WL0005'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality. The single gene may be a naturally occurring watermelon gene or a transgene introduced through genetic engineering techniques.

In another embodiment, the present invention is directed to methods for developing watermelon plants in a watermelon plant breeding program using plant breeding techniques including recurrent selection, backcrossing, pedigree breeding, restriction fragment length polymorphism enhanced selection, genetic marker enhanced selection, and transformation. Marker loci such as restriction fragment polymorphisms or random amplified DNA have been published for many years and may be used for selection (See, Pierce et al., *HortScience* (1990) 25:605-615; Wehner, T., *Cucurbit Genetics Cooperative Report*, (1997) 20: 66-88; and Kennard et al., *Theoretical Applied Genetics* (1994) 89:217-224). Seeds, watermelon plants, and parts thereof produced by such breeding methods are also part of the invention. In addition, any reversion of the tetraploid to diploid is included as part of this invention, because this is a routine natural process (conversion from 4n to 2n ploidy level) seen at a low percentage with any tetraploid.

In additional embodiments, the present invention is directed to watermelon seeds resulting from methods of making a watermelon line of the present invention. In additional embodiments, the present invention is directed to watermelon plants, and parts thereof, obtained from growing the seeds of the present invention. In additional embodiments, the present invention is directed to watermelon plants, and parts thereof, having all the physiological and morphological characteristics of the watermelon plants of the present invention. In additional embodiments, the present invention is directed to watermelon tissue culture, obtained from the plants of the present invention. In further embodiments, the tissue culture of the present invention is produced from a plant part selected from the group consisting of leaf, anther, pistil, stem, petiole, root, root tip, fruit, seed, flower, cotyledon, hypocotyl, embryo, and meristematic cell.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION OF THE INVENTION

Figure 1:
FIG. 1 shows longitudinal cross-sections of fruit of watermelon line 'WL0005' (19-2868).

The present invention is directed towards watermelon varieties exhibiting desired rind, flesh, size, and shape characteristics. These desired rind, flesh, size, and shape characteristics can be accomplished by crossing two watermelon plants such that the progeny watermelon plants exhibit rind, flesh, size, and shape characteristics of both parent plants. In an exemplary embodiment, the present invention is directed towards tetraploid watermelon plants that can be used to breed triploid, seedless, watermelon plants.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits, and then through selection, varieties or parent lines are developed. The goal is to combine in a single line, variety, or hybrid an improved combination of desirable traits from the parental germplasm. These important traits may include higher yield, field performance, resistance to diseases and insects, and tolerance to drought and heat. These important traits may also include fruit and agronomic quality such as fruit shape, fruit appearance, fruit flesh firmness, and internal quality of fruit.

Choice of breeding or selection methods can depend on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for at least three years. The best lines can then be candidates for new commercial cultivars. Those still deficient in a few traits may be used as parents to produce new populations for further selection. These processes, which lead to the final step of marketing and distribution, may take from ten to twenty years from the time the first cross or selection is made.

One goal of watermelon plant breeding is to develop new, unique, and genetically superior watermelon cultivars and hybrids. A breeder can initially select and cross two or more parental lines, followed by repeated selfing and selection, producing many new genetic combinations. A plant breeder can then select which germplasms to advance to the next generation. These germplasms may then be grown under different geographical, climatic, and soil conditions, and further selections can be made during, and at the end of, the growing season.

The development of commercial watermelon cultivars thus requires the development of watermelon parental lines, the crossing of these lines, and the evaluation of the crosses. Pedigree breeding and recurrent selection breeding methods may be used to develop cultivars from breeding populations. Breeding programs can be used to combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs, which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into watermelon varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid, or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., *Theor. Appl. Genet.*, 77:889-892, 1989.

Additional non-limiting examples of breeding methods that may be used include, without limitation, those found in *Principles of Plant Breeding*, John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999.

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Androecious plant. A plant having staminate flowers only.

Anthracnose. Anthracnose of cucurbits is a disease caused by the fungus *Colletotrichum orbiculare* (also called *Colletotrichum lagenarium*). Infected plants have lesions on leaves, stems, and fruits.

Backcrossing. Backcrossing is a process in which a breeder repeatedly crosses hybrid progeny back to one of the parents, for example, a first generation hybrid $F_1$ with one of the parental genotype of the $F_1$ hybrid.

Blossom end. The blossom end is the distal end of the fruit (the "far" end as measured from the base of the plant) where the flower blossom is located. The other end of a fruit is the stem end.

Blossom scar. The blossom scar is the small mark left on the distal end of the fruit after the flower falls off.

Covered cultivation. Any type of cultivation where the plants are not exposed to direct sunlight. The covering includes but is not limited to greenhouses, glasshouses, nethouses, plastic houses, and tunnels.

Essentially all the physiological and morphological characteristics. A plant having essentially all the physiological and morphological characteristics means a plant having the physiological and morphological characteristics of the recurrent parent, except for the characteristics derived from the converted gene.

Fusarium wilt. Fusarium wilt of watermelon is a disease caused by the fungus *Fusarium oxysporum* f. sp. *niveum* (FON). Infected plants wilt, have brown-streaked vascular tissue, and produce small and misshapen fruit.

Gene. As used herein, "gene" refers to a segment of nucleic acid. A gene can be introduced into a genome of a species, whether from a different species or from the same species, using transformation or various breeding methods.

Gynoecious plant. A plant having pistillate flowers only.

Monoecious plant. A plant having separate staminate and pistillate flowers on the same plant.

Percent Identity. Percent identity as used herein refers to the comparison of the homozygous alleles of two watermelon lines, hybrids or varieties. Percent identity is determined by comparing a statistically significant number of the homozygous alleles of two developed varieties, lines or hybrids. For example, a percent identity of 90% between watermelon plant 1 and watermelon plant 2 means that the two plants have the same allele at 90% of their loci.

Propagate. To "propagate" a plant means to reproduce the plant by means including, but not limited to, seeds, cuttings, divisions, tissue culture, embryo culture, or other in vitro method.

Quantitative Trait Loci (QTL). Quantitative trait loci refer to genetic loci that control to some degree numerically representable traits that are usually continuously distributed.

Regeneration. Regeneration refers to the development of a plant from tissue culture.

Seedless. Seedless plants refer to triploid watermelon plants that produce fruit without viable seeds. These fruit may be devoid of seeds or seed-like structures, or may contain immature white ovules.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique, genetic engineering, or mutation.

Transgene. A "transgene" is a gene taken or copied from one organism and inserted into another organism. A transgene may be a gene that is foreign to the receiving organism or it may be a modified version of a native, or endogenous, gene.

Overview of the Watermelon Line 'WL0005'

Watermelon line 'WL0005' is a tetraploid inbred watermelon line that produces round large fruit with firm flesh and light green rind that only has vein pattern. 'WL0005' is suitable for cultivation in the open. FIG. 1 depicts fruit of watermelon line 'WL0005'. Watermelon line 'WL0005' is the result of numerous generations of plant selections chosen for its rind color and pattern, flesh color, flesh firmness, and holding ability in the field.

The line has shown uniformity and stability for the traits, within the limits of environmental influence for the traits. It has been self-pollinated a sufficient number of generations with careful attention to uniformity of plant type. The line has been increased with continued observation for uniformity. No variant traits have been observed or are expected in line 'WL0005'.

Objective Description of the Line 'WL0005'

Figure 2:
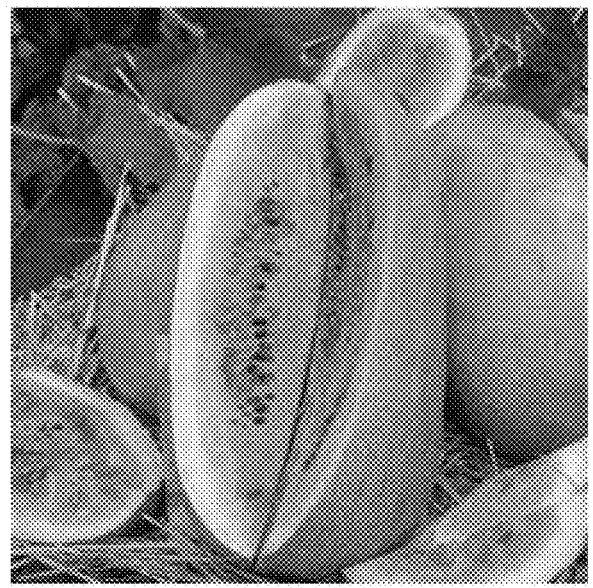
FIG. 2 shows sections of fruit and whole fruit of watermelon variety 'Charleston Gray'.

Watermelon line 'WL0005' has the following morphologic and other characteristics:

General fruit type: Round large
Type of culture: In the open
Maturity:
Number of days from emergence to anthesis: 35 days
Number of days from pollination to maturity: 50 days
Maturity category: Late
Ploidy: Tetraploid
Plant:
Plant sex form: Monoecious
Stem:
Shape in cross-section: Round
Surface: Pubescent
Leaf:
Lobes: Present
Size: Longer than wide
Dorsal surface pubescence: Present
Dorsal surface color: Medium green
Ventral surface pubescence: Present
Ventral surface color: Medium green
Vine color: Green
Flower:
Color: Yellow
Fruit:
Shape: Round
Length: 22 cm
Diameter at midsection: 22 cm
Average weight: 5 kg
Surface: Smooth
Waxy layer: Absent
Skin color pattern: Only veins on solid background
Primary color (ground color): Light green
Conspicuousness of veining: Medium
Pattern of stripes: Only veins
Conspicuousness of stripes: Inconspicuous or very weakly conspicuous
Rind:
Texture: Tough
Thickness of blossom end: 14 mm
Thickness of sides: 17 mm
Flesh:
Texture: Crisp
Coarseness: Fine-little fiber
Color: Red
Hollow heart: 0%
Placental separation: 0%
Transverse crack: 0%
Seeds used to grow plants of the candidate line:
Size: Medium
Length: 9 mm
Width: 6 mm
Thickness: 3 mm
Weight per 1000 seeds: 65 g
Number of seeds per fruit: 50
Color: Dark brown mottled
Seeds produced by the candidate line:
Length: 9 mm
Width: 6 mm
Thickness: 3 mm
Ground color of testa: Brown
Over color of testa: Present
Area of over color in relation to that of ground color: Medium
Patches at hilum: Medium Comparisons to Other Watermelon Varieties Table 1 below compares some of the characteristics of the tetraploid watermelon line 'WL0005' with the commercial watermelon variety 'Charleston Gray' (unpatented). The fruit of variety 'Charleston Gray' has a similar rind pattern to fruit of 'WL0005'. Column 1 lists the characteristic, column 2 shows the characteristics for tetraploid watermelon line 'WL0005', and column 3 shows the characteristics for commercial watermelon variety 'Charleston Gray'. Additional distinguishing characteristics can be determined from the comparison of FIG. 1 ('WL0005') and FIG. 2 ('Charleston Gray').

TABLE 1

| Characteristic | 'WL0005' | 'Charleston Gray' |
| --- | --- | --- |
| Flesh color | Red | Pink |
| Ploidy | Tetraploid | Diploid |
| Fruit shape | Round | Oblong |

Figure 3:
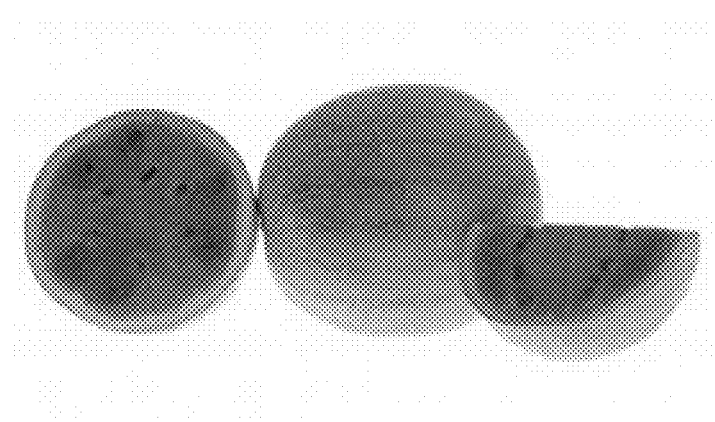
FIG. 3 shows sections of fruit and whole fruit of watermelon variety 'Mickeylee'.

Table 2 below compares some of the characteristics of the tetraploid watermelon line 'WL0005' with the commercial watermelon variety 'Mickeylee' (unpatented). The fruit of variety 'Mickeylee' is round in shape and has a similar rind pattern to fruit of 'WL0005'. Column 1 lists the characteristic, column 2 shows the characteristics for tetraploid watermelon line 'WL0005', and column 3 shows the characteristics for commercial watermelon variety 'Mickeylee'. Additional distinguishing characteristics can be determined from the comparison of FIG. 1 ('WL0005') and FIG. 3 ('Mickeylee').

TABLE 2

| Characteristic | 'WL0005' | 'Mickeylee' |
| --- | --- | --- |
| Flesh color | Red | Pink |
| Ploidy | Tetraploid | Diploid |
| Seed size | Medium | Small |

FURTHER EMBODIMENTS

This invention also is directed to methods for producing a watermelon plant by crossing a first diploid parent watermelon plant with a second tetraploid parent watermelon plant to produce a triploid offspring watermelon plant. In some embodiments, the tetraploid parent plant has light green rind with only vein pattern, red flesh color, firm flesh, and good holding ability in the field. In some embodiments, the tetraploid parent is 'WL0005'.

As used herein, the term plant includes plant cells, plant protoplasts, plant cell tissue cultures from which watermelon plants can be regenerated, plant calli, plant clumps and plant cells that are intact in plants or parts of plants, such as embryos, pollen (pollen grains), ovules, flowers, leaves, stems, and the like.

Genetic Marker Profile Through SSR and First Generation Progeny

In addition to phenotypic observations, a plant can also be identified by its genotype. The genotype of a plant can be characterized through a genetic marker profile which can identify plants of the same or a related variety or line, or can be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et al., "An Integrated Genetic Linkage Map of the Soybean Genome" Crop Science 39:1464-1490 (1999), and Berry et al., "Assessing Probability of Ancestry Using Simple Sequence Repeat Profiles: Applications to Maize Inbred Lines and Soybean Varieties" Genetics 165:331-342 (2003), each of which are incorporated by reference herein in their entirety.

Particular markers used for these purposes are not limited to any particular set of markers, but are envisioned to include any type of marker and marker profile which provides a means of distinguishing varieties.

The present invention includes a watermelon plant characterized by molecular and physiological data obtained from the representative sample of said line deposited with the National Collection of Industrial, Food and Marine Bacteria Ltd. (NCIMB Ltd.). Further provided by the invention is a watermelon plant formed by the combination of the disclosed watermelon plant or plant cell with another watermelon plant or cell and including the homozygous alleles of the line.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by polymerase chain reaction (PCR), thereby eliminating the need for labor-intensive Southern hybridization. PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, include the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Single-Gene Conversions

When the terms watermelon plant, cultivar, hybrid, or watermelon line are used in the context of the present invention, this also includes any single gene conversions of that line. The term "single gene converted plant" as used herein refers to those watermelon plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present invention to improve or introduce a characteristic into the line. The term "backcrossing" as used herein refers to the repeated crossing of a hybrid progeny back to one of the parental watermelon plants for that line, backcrossing 1, 2, 3, 4, 5, 6, 7, 8, or more times to the recurrent parent. The parental watermelon plant which contributes the gene for the desired characteristic is termed the nonrecurrent or donor parent. This terminology refers to the fact that the nonrecurrent parent is used one time in the backcross protocol and therefore does not recur. The parental watermelon plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a watermelon plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross; one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, and examples of these traits include but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability, and yield enhancement. These genes are generally inherited through the nucleus. Several of these single gene traits are described in U.S. Pat. Nos. 5,777,196, 5,948,957 and 5,969,212, the disclosures of which are specifically hereby incorporated by reference.

Tissue Culture

As used herein, the term "tissue culture" indicates a composition including isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture including organs has been used to produce regenerated plants. U.S. Pat. Nos. 5,959,185; 5,973,234 and 5,977,445 describe certain techniques, the disclosures of which are incorporated herein by reference.

Additional Breeding Methods

This invention also is directed to methods for producing a triploid watermelon plant by crossing a tetraploid parent watermelon plant with a diploid parent watermelon plant to generate a triploid watermelon plant. In addition, any reversion of a tetraploid to diploid is included as part of this invention, because this is a routine natural process (conversion from 4n to 2n ploidy level) seen at a low percentage with any tetraploid. In this manner, a diverse array of watermelon rind patterns, watermelon flesh color, and watermelon taste may be developed and selected for superior qualities including appearance and taste. Further, watermelon varieties may be developed and selected for superior qualities including improved firmness of flesh, improved internal quality, increased yield, and hardiness. Breeding steps that may be used in the watermelon plant breeding program include pedigree breeding, backcrossing, mutation breeding, and recurrent selection. In conjunction with these steps, techniques such as RFLP-enhanced selection, genetic marker enhanced selection (for example SSR markers) and the making of double haploids may be utilized.

The cultivar of the invention can also be used for transformation where exogenous genes are introduced and expressed by the cultivar of the invention. Genetic variants of 'WL0005' created either through traditional breeding methods or through transformation of 'WL0005' by any of a number of protocols known to those of skill in the art are intended to be within the scope of this invention.

Mutations for use in mutation breeding can be induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in a gene of interest can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641), the individual plants that have a mutation in the gene of interest are identified. By screening many plants, a large collection of mutant alleles is obtained, each giving a different effect on gene expression or enzyme activity. The gene expression or protein levels can for example be tested by transcript analysis levels (e.g., by RT-PCR) or by quantification of protein levels with antibodies. Plants with the desired reduced gene expression or reduced protein expression are then back-crossed or crossed to other breeding lines to transfer only the desired new allele into the background of the crop wanted.

Genes of interest for use in breeding may also be edited using gene editing techniques including transcription activator-like effector nuclease (TALEN) gene editing techniques, clustered Regularly Interspaced Short Palindromic Repeat (CRISPR/Cas9) gene editing techniques, and/or zinc-finger nuclease (ZFN) gene editing techniques. For this, transgenic plants are generated expressing one or more constructs targeting the gene of interest. These constructs may include, without limitation, an anti-sense construct, an optimized small-RNA construct, an inverted repeat construct, a targeting construct, a guide RNA construct, a construct encoding a targeting protein, and/or a combined sense-anti-sense construct, and may work in conjunction with a nuclease, an endonuclease, and/or an enzyme, so as to downregulate the expression of a gene of interest.

One of ordinary skill in the art of plant breeding would know how to evaluate the traits of two plant varieties to determine if there is no significant difference between the two traits expressed by those varieties. For example, see Fehr and Walt, Principles of Cultivar Development, p. 261-286 (1987). Thus the invention includes watermelon plants including a combination of at least two traits selected from the combination of traits listed in the Summary of the Invention for 'WL0005', so that said progeny watermelon plant is not significantly different for said traits than watermelon 'WL0005', as determined at the 5% significance level when grown in the same environmental conditions and/or may be characterized by percent similarity or identity to watermelon 'WL0005', as determined by SSR markers. Mean trait values may be used to determine whether trait differences are significant, and preferably the traits are measured on plants grown under the same environmental conditions. Once such a variety or line is developed its value is substantial since it is important to advance the germplasm base as a whole in order to maintain or improve traits such as firmness of flesh, internal quality, taste, appearance, yield, disease resistance, pest resistance, and plant performance in extreme environmental conditions.

As used herein, the term "plant" includes plant cells, plant protoplasts, plant cell tissue cultures from which watermelon plants can be regenerated, plant calli, plant clumps, and plant cells that are intact in plants or parts of plants, such as leaves, pollen, embryos, cotyledons, hypocotyl, roots, root tips, anthers, pistils, flowers, seeds, stems, and the like.

The use of the terms "a," "an," and "the," and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the watermelon line 'WL0005' is maintained by Enza Zaden USA, Inc., having an address at 7 Harris Place, Salinas, Calif. 93901, USA. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the line will be irrevocably removed by affording access to a deposit of at least 2,500 seeds of the same line with the National Collection of Industrial, Food and Marine Bacteria Ltd. (NCIMB Ltd), Ferguson Building, Craibstone Estate, Bucksburn, Aberdeen, AB21 9YA, United Kingdom.

At least 2500 seeds of watermelon line 'WL0005' were deposited on Aug. 19, 2020 according to the Budapest Treaty in the National Collection of Industrial, Food and Marine Bacteria Ltd. (NCIMB Ltd), Ferguson Building, Craibstone Estate, Bucksburn, Aberdeen, AB21 9YA, United Kingdom. The deposit has been assigned NCIMB Number 43650. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the line will be irrevocably removed.

The deposit will be maintained in the NCIMB depository, which is a public depository, for a period of 30 years, or 5 years after the most recent request, or for the effective life of the patent, whichever is longer, and will be replaced if a deposit becomes nonviable during that period.

The invention claimed is:

1. A watermelon seed designated as 'WL0005', a representative sample of seed having been deposited under NCIMB Accession Number 43650.

2. A watermelon plant produced by growing the seed of claim 1.

3. A plant part from the plant of claim 2, wherein said part is a fruit.

4. A watermelon plant having all the physiological and morphological characteristics of the watermelon plant of claim 2.

5. A plant part from the plant of claim 4, wherein said part is a fruit.

6. A pollen grain or an ovule of the plant of claim 2.

7. A watermelon plant regenerated from a tissue culture of the plant of claim 2, wherein the tissue culture is produced from a plant part selected from the group consisting of leaf, anther, pistil, stem, petiole, root, root tip, fruit, flower, cotyledon, hypocotyl, and meristematic cell, and wherein the plant has all of the morphological and physiological characteristics of a watermelon plant produced by growing watermelon seed designated as 'WL0005', a representative sample of seed having been deposited under NCIMB Accession Number 43650.

8. A method of producing watermelon seed, the method comprising:
    (a) crossing a 'WL0005' watermelon plant, a representative sample of seed having been deposited under NCIMB Accession Number 43650, with a diploid watermelon plant; and
    (b) harvesting the resulting triploid seed.

* * * * *